Dec. 6, 1960 G. J. VON ABRAMS Plant Pat. 1,991
ROSE PLANT
Filed Jan. 22, 1960
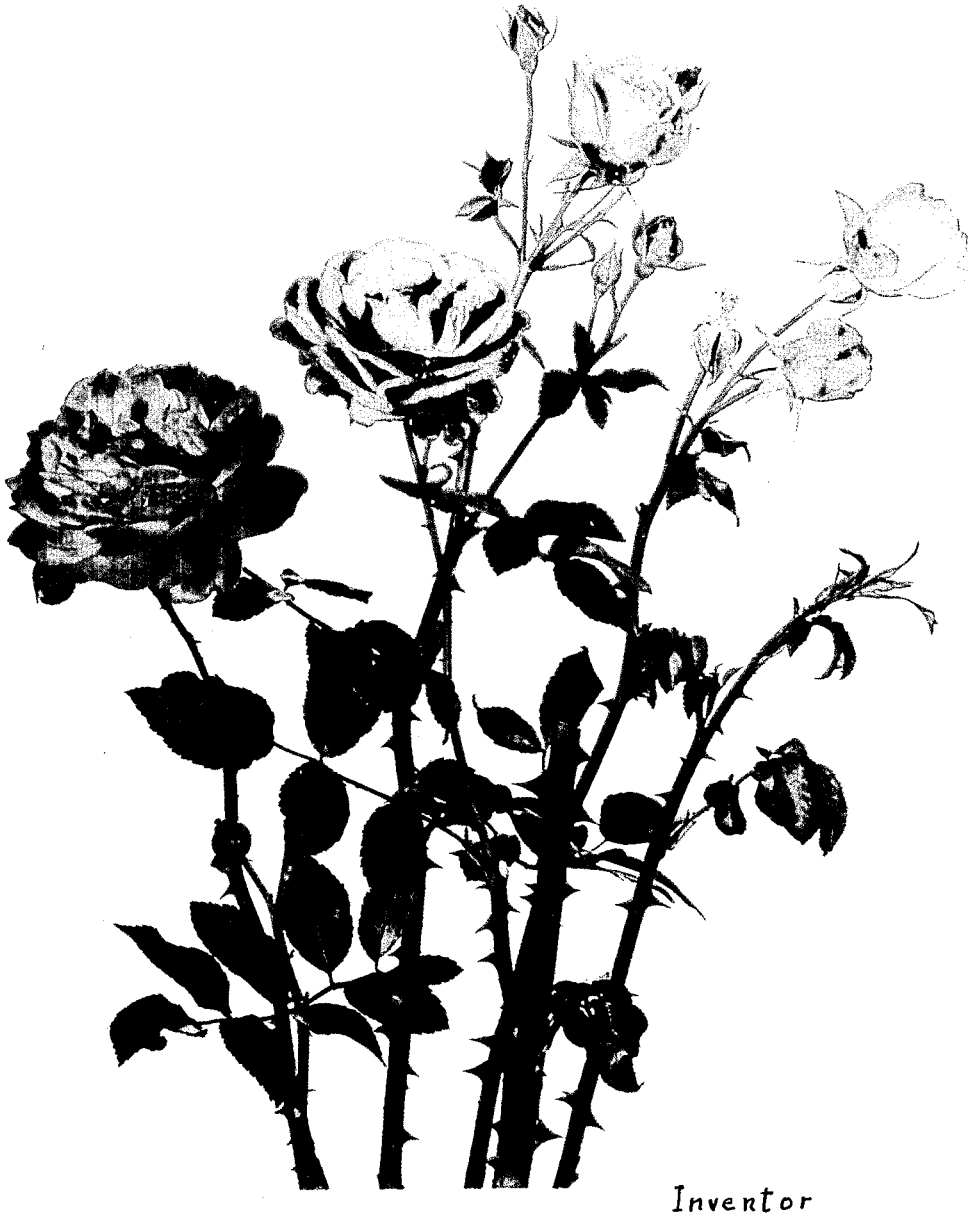
Inventor
Gordon J. Von Abrams
by F. H. Geisler.
Attorney.

United States Patent Office

Plant Pat. 1,991
Patented Dec. 6, 1960

1,991

ROSE PLANT

Gordon J. Von Abrams, Portland, Oreg., assignor to Eldon Pinkeney Dering, Scappoose, Oreg.

Filed Jan. 22, 1960, Ser. No. 4,163

1 Claim. (Cl. 47—61)

The present invention relates to a new and distinct variety of rose plant of the commercial floribunda class in a compact bush-type, originated by me as a result of the pollination of the "Else Poulsen," unpatented, with another variety of rose which is not commercially known and which had previously been originated by me through pollination of the "Fashion" (Plant Patent No. 789) with the variety "Orange Triumph," unpatented, the breeding of the rose plant of the present invention having been carried out with definite objectives in mind. Among the objectives which were obtained, and which constitute the principal distinguishing characteristics of the new rose plant of the present invention, are the special combination of flower form and flower color and the unique pattern and sequence of the flower color during maturation and senescence. These characteristics are hereafter described.

The pollination for originating this new rose plant was performed by me in the spring of 1951 at Scappoose, Oregon, the seed planting occurred in the fall of 1951 and the first flower appeared in the spring of 1952. Asexual reproduction through successive propagations by bud-grafting at Scappoose, Oregon, since 1952 have established proof of the fact that this new variety of rose plant retains its distinguishing characteristics through succeeding propagations by bud-grafting.

The new rose plant is clearly distinguished from the following varieties, namely, "Else Poulsen," "Fashion" and "Orange Triumph," in the following particulars:

It is lower and more compact in growth, the flower is larger and has more petals, and the color is deeper with more orange than the "Else Poulsen."

The flower is much darker in color and shows more red than the "Fashion."

The flower is larger, more symmetrical in form and less yellow in color than the pollen parent which resulted from a cross between "Fashion" and "Orange Triumph."

Also the foliage is larger, but less glossy, and the plant is less vigorous and somewhat less disease-resistant than the pollen parent.

The new rose plant to a certain extent bears some resemblance to the "Floradora" (unpatented). Thus it resembles a "Floradora" in general flower color, but the newly opened flower is paler with less red inside. The outer (dorsal) surface of the petals is less blue and the texture is smoother. The fading reaction of the new rose is very different from that of the "Floradora" since the new rose becomes darker and more red under the same conditions which cause the "Floradora" flower to become lighter and bluer. The flower of the new rose is smaller, more open and less cupped than that of the "Floradora," the bud is smaller, showning more orange and less red than in the case of the "Floradora," and the plant of the new rose is lower and more compact than the "Floradora."

The plant of this new variety is a small, compact bush bearing several to many per stem in medium-sized, compact, cymose clusters. The plant blooms abundantly out-of-doors and blooms nearly continuously during the entire growing season. The flowers have a moderate, tea-rose fragrance. The general color effect of the face view of the flowers when newly opening is near Carmine (Wilson 21 to 21/1, page 21). After being opened for a period of three days the general color effect is nearer Carmine Rose (Wilson 621, page 75).

In senescence, particularly under conditions of high temperature and high light intensity, the exposed areas of the inner surface of the petals darkens very markedly to near Currant Red (Wilson 821/2, page 167). The appearance of this area of the petals usually becomes somewhat mottled, with some small markings becoming even darker. At the same time the outer surface of the petals becomes more blue to near Tyrian Rose (Wilson 24/1 to 24/2, page 24). The petals drop cleanly except in extremely wet cool weather. The flowers have been observed to last eight days in moderate outdoors temperature in September and the cut flowers from an outdoor plant have been observed to last seven days inside at room temperature.

The accompanying illustration shows the plant in color with separated blooms in different stages of development.

The following are further details for the description of the new variety, the color terminology being taken from the following standard color references:

(1) Wilson, R. F.—Royal Horticultural Society Colour Chart, England, 1940.

(2) Ridgway, R.—Color Standards and Color Nomenclature, Washington, D.C., 1912.

(3) Nickerson Color Fan, Munsel Color Co., 1957.

Flower: Blooms abundantly, nearly continuously outdoors during growing season.

*Size.*—Small, when fully opened, about 7 cm.

*Form.*—Compact to high centered at first, becoming gradually expanded and more nearly flat at senescence. Petals at first erect, slightly cupped inwardly, gradually roll outwardly at apical-lateral margins.

*Petalage.*—Double, about thirty to thirty-five petals, sometimes as many as forty-five.

Petals: Shiny outside and satiny inside in texture; medium thick, hard, flexible.

*Shape and size.*—Outside petal—broad obovate, about 3.5 by 3.5 cm., with apex slightly emarginate or irregular. Intermediate petal—obovate, about 2.5 by 3 cm., apex slightly emarginate to rounded, not regular. Inside petal—obovate, 2.2 by 2.7 cm., apex irregular.

*Color (when flower newly opened).*—Outside petal—dorsal surface, except for basal fan which is small and near white, this is near Carmine (Wilson 21/1, page 21), sometimes flushed irregularly with Ruby Red (Wilson 827, page 171) or darker; ventral surface, except for basal fan which is small and near white to near Aureolin (Wilson 3/2, page 3), this surface is between Geranium Lake (Wilson 20, page 20) and Carmine (Wilson 21, page 21) near the base, paling to lighter tints at apex (Wilson 20/2, to 21/2, page 21). Intermediate petal—dorsal surface, except for basal fan which is small and near white, this surface is near Carmine (Wilson 21, page 21), to very slightly lighter tint (Wilson 21/1) near apex; ventral surface, except for basal small fan, which is near Aureolin (Wilson 3/2, page 3), this surface is Geranium Lake (Wilson 20, page 20) to slightly lighter tint (Wilson 20/1) near the apex. Inside petal—same as intermediate petal.

*Color (after flower has been opened for three days).*—Outside petal—dorsal surface, basal fan very small near white; rest of surface near Rose Madder (Wilson 23 to 23/1, page 23) frequently flushed irregularly with darker color, near Indian Lake (Wilson 826/3, page 170) or darker; ventral surface, except for basal near white fan, this surface is near Carmine Rose (Wilson 621, page 75) near base flushing upward to Carmine (Wilson 20, page 20) in apical one third or more of the petal. Intermediate petal—dorsal surface, basal fan near white, remainder near Rose Madder (Wilson 23/1 to 23/2, page 23); ventral surface, basal fan near white, remainder near Carmine Rose (Wilson 621, page 75). Inside petal—same as intermediate petal.

Change of color in senescence as described above.

Foliage: Abundant, smooth, glossy, medium-small (from 2.7 cm. by 5 cm., or smaller); long ovate, near oval; base rounded to near acute, tip acute, margin simply serrate sometimes irregular.

Color of foliage:

*Mature.*—Upper surface near Spinach Green (Wilson 0960, page 187) to darker; under surface near Bice Green (Ridgway 29′, G G–Y, *k* Plate XVII).

*Young.*—Upper surface near Diamine Brown (Ridgway 3′ O–R. *m*, Plate XIII) flushed near Parrot Green (Ridgway 31. Y–G. *k*, Plate VI) from mid-rib; under surface, near Vandyke Red (Ridgway 1′. RED. *k*, Plate XIII) flushed greenish near mid-rib.

Plant form: Compact, much branched.

Having thus disclosed my invention, I claim:

A new and distinct variety of compact bush type floribunda rose plant, substantially as described, having cymose clusters of medium-sized, compact flowers, blooming abundantly and continuously outdoors during the growing season, and characterized particularly by a special combination of flower form and color and by the unique pattern and sequence of the flower color during maturation and senescence.

No references cited.